US011518698B2

(12) United States Patent
Zenki et al.

(10) Patent No.: US 11,518,698 B2
(45) Date of Patent: Dec. 6, 2022

(54) MICROORGANISM IMMOBILIZED CARRIER

(71) Applicant: TOYO TANSO CO., LTD., Osaka (JP)

(72) Inventors: Masashi Zenki, Osaka (JP); Tetsuro Tojo, Osaka (JP); Masatoshi Takeshita, Osaka (JP); Tomoya Nakazono, Osaka (JP); Ai Ishikawa, Osaka (JP)

(73) Assignee: TOYO TANSO CO., LTD., Osaka (JP)

( * ) Notice: Subject to any disclaimer, the term of this patent is extended or adjusted under 35 U.S.C. 154(b) by 165 days.

(21) Appl. No.: 16/772,050

(22) PCT Filed: Dec. 13, 2018

(86) PCT No.: PCT/JP2018/045853
§ 371 (c)(1),
(2) Date: Jun. 11, 2020

(87) PCT Pub. No.: WO2019/117242
PCT Pub. Date: Jun. 20, 2019

(65) Prior Publication Data
US 2021/0171373 A1 Jun. 10, 2021

(30) Foreign Application Priority Data

Dec. 13, 2017 (JP) .............................. JP2017-238690

(51) Int. Cl.
  *C02F 3/10* (2006.01)
  *C12N 11/02* (2006.01)
  *C12N 1/20* (2006.01)
(52) U.S. Cl.
  CPC ............... *C02F 3/107* (2013.01); *C12N 1/20* (2013.01); *C12N 11/02* (2013.01)
(58) Field of Classification Search
  CPC .......... C02F 3/104; C02F 3/106; C02F 3/107; C02F 3/108; C02F 3/302
  (Continued)

(56) References Cited

U.S. PATENT DOCUMENTS 5,894,696 A * 4/1999 Ando ..................... A01G 7/02
                                                         205/555
5,980,738 A * 11/1999 Heitkamp ............. C12N 11/00
                                                         210/150
(Continued)

FOREIGN PATENT DOCUMENTS

CN          103524648 A       1/2014
CN          107311297 A       11/2017
(Continued)

OTHER PUBLICATIONS

Niimi, JP 2015124306, English machine translation, pp. 1-25 (Year: 2015).*

(Continued)

*Primary Examiner* — Claire A Norris
(74) *Attorney, Agent, or Firm* — Rankin, Hill & Clark LLP

(57) ABSTRACT

[Problem] A microorganism immobilized carrier is provided that is easy for microorganisms to adhere to, and is able to reduce the manufacturing cost of the microorganism immobilized carrier and the running cost of an apparatus that uses the microorganism immobilized carrier.

[Solution] A microorganism immobilized carrier is characterized by including a carbon component and a resin, having a zeta potential of from −25 mV to 0 mV, and containing microorganisms adhered to a surface thereof and/or an interior thereof. The microorganisms are preferably nitrifying bacteria. The carbon component preferably has a particle size of from 1 μm to 1000 μm.

9 Claims, 1 Drawing Sheet

(58) Field of Classification Search
USPC .................................................. 210/616, 610
See application file for complete search history.

(56) References Cited

U.S. PATENT DOCUMENTS

| 6,372,138 B1 * | 4/2002 | Cho .......................... C02F 3/30 |
| | | 210/615 |
| 2002/0149656 A1 | 10/2002 | Nohr et al. |
| 2004/0253447 A1 | 12/2004 | Ogura et al. |

FOREIGN PATENT DOCUMENTS

| JP | 62-296878 A | | 12/1987 |
|----|----|----|----|
| JP | 64-4292 A | | 1/1989 |
| JP | 8-331999 A | | 12/1996 |
| JP | 2001-205288 A | | 7/2001 |
| JP | 2005-66595 A | | 3/2005 |
| JP | 2010-42395 A | | 2/2010 |
| JP | 2015-71157 A | | 4/2015 |
| JP | 2015124306 A | * | 7/2015 |
| WO | 92/00799 A1 | | 1/1992 |

OTHER PUBLICATIONS

"Application of the Activated Carbon", website of Osaka Gas Chemicals Co., Ltd., 2018, total 4 pages; English machine translation of relevant information; Cited in An Offer of Information.

An Offer of Information dated Jul. 26, 2021 for corresponding Japanese Patent Application No. 2017-238690 submitted in JPO.

"Development of technology to utilize useful microorganisms for nitrogen treatment of sewage and industrial wastewater", New Age of University, Innovative University, Nikkei Business, Dec. 2015 and Jan. 2016, vol. 9, total 5 pages; English machine translation; Cited in Specification.

International Search Report (ISR) dated Mar. 5, 2019 issued in PCT/JP2018/045853.

Japanese Office Action (JPOA) dated Jan. 14, 2022 for corresponding Japanese Patent Application No. 2017-238690 and its English translation.

Singapore Office Action (SGOA) dated Sep. 15, 2021 issued in corresponding Singapore Patent Application No. 11202005508U.

A Third Party Submission dated Oct. 4, 2022 for Japanese Patent Application No. 2022-057625.

* cited by examiner

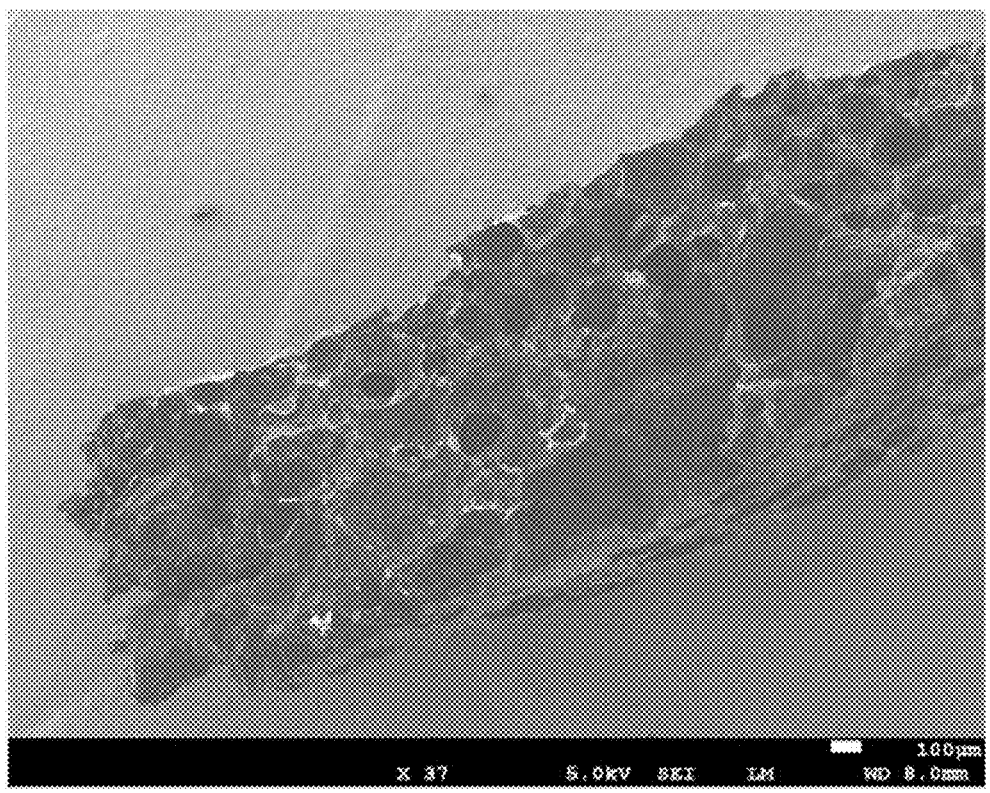

MICROORGANISM IMMOBILIZED CARRIER

TECHNICAL FIELD

The present invention relates to a microorganism immobilized carrier containing a carbon component and a resin, more particularly to one that is used as a microorganism immobilized carrier to which microorganisms are adhered when biochemically performing a wastewater treatment.

BACKGROUND ART

A cause of eutrophication is that nitrogen and phosphorus that have been contained in domestic wastewater, industrial wastewater, and agricultural wastewater remain within closed water in the natural world. Among approximately 2,200 sewage treatment plants throughout the whole country, only approximately 100 plants are able to perform a sufficient nitrogen treatment (see Non-patent literature 1).

Examples of the treatment methods for nitrogen contained in wastewater include catalyst degradation methods, direct combustion methods, hypochlorous acid impregnation methods, and biodegradation methods. In many cases, the biodegradation methods are utilized particularly for decomposition of ammonia nitrogen at 1 to 1,000 ppm, partly because of cost considerations. A wastewater treatment using a biodegradation method is a technique of clarification of water by causing microorganisms adhered to an immobilized carrier (hereinafter also referred to simply as "carrier") to decompose the organic substances and nitrogen contained wastewater.

Examples of the materials used for the above-described carrier for attachment of microorganisms include plastic materials, inorganic materials, entrapping gel materials, and hydrophilic gel materials. In addition, mixing of the above-described materials with another material has been investigated to achieve an increase in the amount of immobilized microorganisms, adjustment of the specific gravity, improvement in the strength, and cost reduction originating from the use of general-purpose materials.

When microorganisms adhere to the carrier more quickly, the initial decomposition rate of the microorganisms accordingly becomes faster. For this reason, it is necessary to use a carrier that is easier for microorganisms to adhere to. Therefore, it is desired to use, for example, a material that shows high affinity with microorganisms, a material that has a smaller energy barrier with the microorganisms, and a material having many hydrophilic groups on the carrier surface.

Moreover, lighter materials are desired for fluid bed carriers. The reason is that reducing the weight of the carrier improves the flowability in water, making it possible to reduce the necessary mechanical power for agitation and aeration. Furthermore, when a material with a higher porosity is used for the carrier, the immobilized sites for microorganisms are increased, so it is expected to increase the number of microorganisms accordingly.

In addition, because a wastewater treatment utilizing biodegradation requires a large amount of carriers, it is necessary to take the corresponding manufacturing cost into consideration sufficiently. This means that it is desirable to use a material that are as low-cost as possible, such as a general-purpose material and a waste material.

Patent Literature 1 listed below discloses a microorganism immobilized carrier containing a thermoplastic resin (particularly polypropylene) as its main component, a carbonaceous filler or a glass filler in an amount of 0.1% to 5%, wherein the filler size is from 50 μm to 3000 μm.

Patent Literature 2 listed below discloses a microorganism immobilized carrier that is produced by carbonizing a formed material of an aggregate employing one or more carbonaceous substances selected from natural graphite, artificial graphite, carbon fiber, coke, carbon black, and precursors thereof, in which the surface area of the formed material is 400 m$^2$/g or less.

CITATION LIST

Patent Literature

[Patent Literature 1] Japanese Published Unexamined Patent Application No. 2015-71157
[Patent Literature 2] Japanese Published Unexamined Patent Application No. S62-296878

Non-Patent Literature

[Non-patent Literature 1] Nikkei Business (Dec. 28, 2015 and Jan. 4, 2016 issues)

SUMMARY OF INVENTION

Technical Problem

However, Patent Literature 1 describes that the microorganism immobilized carrier should preferably contain a resin in an amount of 70 mass % or more. This means that the carrier is resin-rich and is difficult for microorganisms to adhere to. Another problem is that carbon fibers and activated carbon fibers are costly for use as a material for the carrier.

The microorganism immobilized carrier of Patent Literature 2 is produced by carbonizing or graphitizing a formed material of an aggregate employing one or more carbonaceous substances selected from natural graphite, artificial graphite, carbon fiber, coke, carbon black, and precursors thereof. Therefore, the bulk density of the carrier is believed to be at least 1.3 or higher, which means that the carrier will require a large amount of energy when it needs to flow inside a tank and that running cost will be high.

The present invention has been accomplished in view of the foregoing circumstances, and it is an object of the invention to provide a microorganism immobilized carrier that is easy for microorganisms to adhere to, and to reduce the manufacturing cost of the microorganism immobilized carrier and the running cost of an apparatus that uses the microorganism immobilized carrier.

Solution to Problem

An embodiment of the present invention provides a microorganism immobilized carrier characterized by comprising a carbon component and a resin, having a zeta potential of from −25 mV to 0 mV, and containing microorganisms adhered to a surface thereof and/or an interior thereof.

Advantageous Effects of Invention

The present invention achieves significant advantageous effects of allowing microorganisms to easily adhere to the microorganism immobilized carrier, and also reducing the manufacturing cost of the microorganism immobilized carrier or the like.

BRIEF DESCRIPTION OF DRAWINGS

FIG. 1 is a cross-sectional SEM image of a carrier A1.

DESCRIPTION OF EMBODIMENTS

A microorganism immobilized carrier is characterized by comprising a carbon component and a resin, having a zeta potential of from −25 mV to 0 mV, and containing microorganisms adhered to a surface thereof and/or an interior thereof.

In the present invention, the term "carbon component" refers to a carbon nano material and a carbon material other than carbon fibers.

When the zeta potential is from −25 mV to 0 mV as in the just-described configuration, the deviation from the zeta potential of microorganisms is small (for example, the zeta potential of nitrifying bacteria is about −22 mV to −27 mV), so it is easier to cause interaction. As a result, a large number of microorganisms can be adhered to the microorganism adhered carrier. Moreover, because the carrier is a mixture of a carbon component and a resin, it is possible to reduce the manufacturing cost (i.e., the material cost) of the microorganism adhered carrier. In particular, for the wastewater treatment plant that uses a large amount of microorganism adhered carrier, the effect of cost reduction is extremely significant.

In addition, the carbon component shows high physical strength and high chemical stability relative to the resin. For this reason, when the carbon component is added as a filler or the like, the strength of the microorganism adhered carrier in water is improved. It should be noted that the just-mentioned microorganisms include nitrifying bacteria mentioned below, but do not include anammox bacteria.

It is desirable that the microorganism be aerobic. An aerobic microorganism requires aeration. However, the microorganism immobilized carrier of the present invention shows high physical strength and high chemical stability as described above, making it possible to exhibit its advantages more significantly.

It is more desirable that the aerobic microorganism be nitrifying bacteria. The use of nitrifying bacteria makes it possible to carry out the wastewater treatment and the like smoothly. Examples of the nitrifying bacteria include ammonia oxidizing bacteria and nitrite oxidizing bacteria.

It is desirable that the carbon component have a particle size of from 1 µm to 1000 µm, more desirably from 2 µm to 500 µm.

Addition of the carbon component with such a wide particle size distribution as a filler or the like improves the strength of the carrier in water. In addition, when the carrier surface has a large number of pores of varying sizes, it is possible that many kinds of microorganisms can form a biofilm efficiently. Although it is preferable that the particle size distribution of the carbon component be 2 µm to 500 µm, the particle size distribution is not limited to this range. The advantageous effect of the present invention can be obtained when the particle size is distributed widely within the range of 1 µm to 1000 µm, such as 3 µm to 600 µm, 4 µm to 700 µm, and 1 µm to 400 µm. In order to distribute the carbon component widely, it is desirable that the lower limit of the particle size be 10 µm or less (when the just-mentioned range is also taken into consideration, the lower limit of the particle size should be from 1 µm to 10 µm), and it is desirable that the upper limit of the particle size be 300 µm or greater (when the just-mentioned range is taking into consideration, the upper limit of the particle size should be from 300 µm to 1000 µm).

It is desirable that the carbon component be graphite. It is particularly desirable that the carbon component be isotropic graphite. The reason why graphite, particularly isotropic graphite, is desirable as the carbon component is that graphite, particularly isotropic graphite, is able to obtain the above-described actions and advantageous effects smoothly, and is also able to reduce the manufacturing cost of the microorganism immobilized carrier because it is low in cost. Examples of the carbon component include graphite, activated carbon, and carbon black. Examples of the graphite include artificial graphite and natural graphite. Examples of the artificial graphite include isotropic graphite and anisotropic graphite. Examples of the natural graphite include earthy graphite and flake graphite. It is preferable to use these carbon components in powder form or in paste form.

It is desirable that the proportion of the carbon component be from 50 weight % to 75 weight %, and the proportion of the resin be from 20 weight % to 40 weight %.

The just-mentioned proportions of the carbon component and the resin serve to form continuous pores easily, and moreover improve the strength in water. Taking these matters into consideration, it is more preferable that the proportion of the carbon component be from 55 weight % to 70 weight %, and the proportion of the resin be from 25 weight % to 35 weight %. It should be noted that an example of the component other than the carbon component and the resin is a later-described cross-linking agent.

It is desirable that the interior of the microorganism immobilized carrier include continuous pores, and the pores have a diameter of from 1 µm to 1000 µm.

The just-mentioned configuration serves to have a larger number of microorganism immobilized sites, enabling a larger number of microorganisms to be adhered to the microorganism immobilized carrier.

OTHER EMBODIMENTS (1) It is preferable to employ a thermoplastic resin as the resin. Examples of the resin include at least one selected from polyvinyl alcohol, polyethylene, polycarbonate, polypropylene, and vinyl chloride. Among the thermoplastic resins, it is preferable to use a thermoplastic resin having a hydroxy group. When the resin has a hydroxy group, hydrophilicity is increased, and affinity of the resin with water is increased. Moreover, it is easier to form pores. An example of the hydrophilic resin having a hydroxy group is polyvinyl alcohol.

(2) It is possible to use a chemical compound having a carboxyl group and/or an aldehyde group as the cross-linking agent for the just-mentioned thermoplastic resin having a hydroxy group. The use of such a chemical compound serves to accelerate the cross-linking reaction of the thermoplastic resin, and makes it possible to produce a more robust formed product. Preferable examples of the chemical compound having a carboxyl group include formic acid, acetic acid, citric acid, and oxalic acid. A preferable example of the chemical compound having an aldehyde group is formaldehyde. The reason is that these chemical compounds are easy to manufacture in a large amount and at low cost. The use of cross-linking agent improves wear resistance.

(3) The microorganism immobilized carrier may take various shapes, such as plate-shaped, cylindrical, corrugated, spherical, hollow tubular, columnar, cuboid, rectangular parallelepiped, and sheet-shaped. By employing any of these shapes, the carrier is able to have a sufficient amount of adhered microorganisms.

EMBODIMENTS

Hereinbelow, a first embodiment and a second embodiment are described. It should be noted, however, that the following embodiments are merely exemplary and the present invention is not limited to the following embodiments.

First Embodiment

Example 1

First, polyvinyl alcohol (available from Wako Pure Chemical Industries Ltd.: degree of polymerization 500, saponification value 86 mole % to 90 mole %, subjected to quantitative restriction such that the proportion of polyvinyl alcohol with respect to the total amount of the microorganism immobilized carrier is 30 weight % after the carrier is manufactured) in a concentration of 30 weight % was mixed with isotropic graphite powder (one type of artificial graphite, available from Toyo Tanso Co., Ltd, particle size: 2 μm to 500 μm) as the carbon component in an amount of 65 weight %, and citric acid (available from Wako Pure Chemical Industries Ltd.) as a cross-linking agent in an amount of 5 weight %, to obtain a paste. Next, the prepared paste was coated onto a mold release paper at a thickness of 2 mm and then dried, and thereafter, using a punch and a mold, a formed product in a pellet form with a diameter of 5 mm and a thickness of 2 mm was obtained. Finally, the formed product was subjected to a heat treatment at 150° C. for 18 hours, to thus prepare a microorganism immobilized carrier.

The microorganism immobilized carrier fabricated in this manner is hereinafter referred to as a carrier A1.

Example 2

A microorganism immobilized carrier was fabricated in the same manner as described in Example 1 above, except that natural graphite (particle size 2 μm to 10 μm) was used as the carbon component.

The microorganism immobilized carrier fabricated in this manner is hereinafter referred to as a carrier A2.

Example 3

A microorganism immobilized carrier was fabricated in the same manner as described in Example 1 above, except that carbon nanotube (diameter 5 μm to 100 μm, length 1 μm to 10 μm) was used as the carbon component.

The microorganism immobilized carrier fabricated in this manner is hereinafter referred to as a carrier A3.

Comparative Example 1

A microorganism immobilized carrier was fabricated in the same manner as described in Example 1 above, except that isotropic graphite powder (available from Toyo Tanso Co., Ltd., particle size: the diameter of the smallest powder particle was greater than 500 μm) was used as the carbon component.

The microorganism immobilized carrier fabricated in this manner is hereinafter referred to as a carrier Z1.

Comparative Example 2

A microorganism immobilized carrier was fabricated in the same manner as described in Example 1 above, except that isotropic graphite powder (available from Toyo Tanso Co., Ltd., particle size: the diameter of the largest powder particle was less than 2 μm) was used as the carbon component.

The microorganism immobilized carrier fabricated in this manner is hereinafter referred to as a carrier Z2.

Comparative Example 3

A microorganism immobilized carrier was fabricated in the same manner as described in Example 1 above, except that the proportion of polyvinyl alcohol was set to 85 weight % and the proportion of isotropic graphite powder was set to 10 weight %.

The microorganism immobilized carrier fabricated in this manner is hereinafter referred to as a carrier Z3.

Comparative Example 4

A microorganism immobilized carrier was fabricated in the same manner as described in Example 1 above, except that the proportion of polyvinyl alcohol was set to 10 weight % and the proportion of isotropic graphite powder was set to 85 weight %.

The microorganism immobilized carrier fabricated in this manner is hereinafter referred to as a carrier Z4.

Comparative Example 5

A microorganism immobilized carrier was fabricated in the same manner as described in Example 1 above, except that phosphoric acid was used as the cross-linking agent.

The microorganism immobilized carrier fabricated in this manner is hereinafter referred to as a carrier Z5.

Experiment

Using the above-described carriers A1 to A3 and Z1 to Z5, experiments were conducted concerning the following sections: (1) Strength in water to (5) Amount of immobilized microorganisms. The results are shown in Table 1 below.

(1) Strength in Water

1 L of water and 100 mL of the carrier were placed in a 1.5-L vessel and stirred at 600 rpm continuously for 24 hours. Then, the abrasion loss was measured by measuring the weight of the carrier after stirring to calculate the weight reduction rate of the carrier from the equation (A) below. The ones that showed a weight reduction rate of less than 0.1% were determined as "very good", the ones that showed a weight reduction rate of equal to or greater than 0.1% to less than 0.3% were determined as "good", the ones that showed a weight reduction rate of equal to or greater than 0.3% to less than 0.5% were determined as "fair", and the ones that showed a weight reduction rate of equal to or greater than 0.5% was determined as "poor".

Weight reduction rate=[(Carrier weight after experiment−Carrier weight before experiment)/Carrier weight before experiment]×100  (A)

(2) Floating Capability in Water

The floating capability of each of the carriers was confirmed by visual observation. The ones that were dispersed uniformly in the vessel were determined as "very good", the ones that were floated mostly were determined as "good", the ones that were floated partially were determined to be "fair", and the ones that were not floated at all were determined as "poor".

(3) Observation of Continuous Pores

The formed product (i.e., carrier) fabricated in the above-described manner was observed with a scanning microscope to observe the surface and a cross section of the carrier (see FIG. 1). The ones observed to have a large number of continuous pores were determined as "very good", the ones observed to have a certain number of continuous pores were determined as "good", and the ones observed to have no continuous pores were determined as "poor".

(4) Measurement of Zeta Potential

The zeta potential was measured in the procedure shown in the following (i) to (iv).

(i) The formed product (carrier) was pulverized into powder form using mortar, and thereafter 1 g of the powdered material (aggregate) was added to 50 mL of water.

(ii) The mixture was stirred with a spoon for 1 minute, and thereafter stirred with an ultrasonic cleaner (ultrasonic cleaner ASU-10 manufactured by AS ONE corp.) at a frequency of 40 Hz and an output power of 240 W for 5 minutes.

(iii) Immediately after the stirring, 1 mL of the supernatant fluid was filled into a dip cell, and the zeta potential was measured using a zeta potential measurement device (Zetasizer Nano ZS90 manufactured by Malvern Ltd.) with a red laser at a wavelength of 633 nm. The pH at the time of measurement was 7. The measurement was carried out three times, and the average value was employed as the zeta potential of the carrier.

(5) Measurement of Amount of Immobilized Microorganism (the Number of Copies of Target gene per 1 g of carrier)

Inorganic synthetic wastewater ($NH_4$—N 40 mg/L) was continuously introduced as a raw water into a 1-L vessel to conduct the treatment. 10 mL of the carrier was added thereto, and a treatment operation was performed for 150 days while aeration was being performed. Using the carrier thus prepared and setting ammonia oxidizing bacteria as the target bacteria, real-time PCR analysis was conducted. At this time, the target was set to ammonia oxidase gene amoA and nitrite oxidoreductase gene norB, which is retained by nitrite oxidizing bacteria, to determine the number of copies of the bacterial per 1 g of the carrier. The DNA extraction was using MORA-EXTRACT kit (Kyokuto Pharmaceutical Industrial Co., Ltd., Tokyo). In the PCR (polymerase chain reaction measurement), the primer was designed to target amoA: amoA-F1, amoA-2R, and norB: NxrBF1, NxrB1R, and standard DNA *Nitrosomonas europaea* NBRC 14298 (for measuring the number of copies of amoA gene), *Nitrobacter winogradskyi* SYBR® Premix Ex TaTM II (Takara, Shiga), MightyAmp® for Real Time (Takara, Shiga) were used. The real-time PCR device used was Rotor-Gene™ Q (Qiagen, Germany).

TABLE 1

| | | Carrier A1 | Carrier A2 | Carrier A3 | Carrier Z1 | Carrier Z2 | Carrier Z3 | Carrier Z4 | Carrier Z5 |
|---|---|---|---|---|---|---|---|---|---|
| Material composition | PVA | 30 | 30 | 30 | 30 | 30 | 85 | 10 | 30 |
| | Isotropic graphite powder (>500 µm) | — | — | — | 65 | — | — | — | — |
| | Isotropic graphite powder (2 µm-500 µm) | 65 | — | — | — | — | 10 | 85 | 65 |
| | Isotropic graphite powder (less than 2 µm) | — | — | — | — | 65 | — | — | — |
| | Natural graphite | — | 65 | — | — | — | — | — | — |
| | Carbon nanotube | — | — | 65 | — | — | — | — | — |
| | Citric acid | 5 | 5 | 5 | 5 | 5 | 5 | 5 | — |
| | Phosphoric acid | — | — | — | — | — | — | — | 5 |
| Physical property | Strength | Very good | Good | Good | Fair | Fair | Good | Poor | Poor |
| | Floating capability | Very good | Good | Good | Good | Good | Good | Poor | Poor |
| | Continuous pores | Very good | Good | Good | Poor | Poor | Poor | Poor | Poor |
| | Zeta potential (mV) | −9.1 mV | −10.1 mV | −9.2 mV | <−25 mV | <−25 mV | <−30 mV | <−25 mV | — |
| | Number of copies of target gene per 1 g of carrier | $1.9 \times 10^9$ | $1.9 \times 10^9$ | $1.9 \times 10^9$ | $1.9 \times 10^8$ | $1.9 \times 10^8$ | $1.9 \times 10^8$ | Unmeasureable | Unmeasureable |

Results of the Experiment

As clearly seen from Table 1, it was observed that the zeta potential of the carriers A1 to A3 was higher, −10.1 mV to −9.1 mV, while the zeta potential of the carriers Z1 to Z4 was lower, less than −25 mV.

For the carriers A1 to A3, the presence of continuous pores of 1 µm to 1000 µm was observed in the surface and the cross section of each carrier. A particularly large number of such pores were observed in the carrier A1. In contrast, for the carriers Z1 to Z4, the absence of continuous pores was observed in the surface and the cross section of each carrier.

As described above, in the carriers A1 to A3, the deviation of zeta potential from the zeta potential of nitrifying bacteria is small. Therefore, in the carriers A1 to A3, microorganisms (ammonia oxidizing bacteria) are easily immobilized to the carrier. Moreover, because the carriers A1 to A3 have a large number of continuous pores, the number of immobilized sites of microorganisms is large. From these points, the carriers A1 to A3 have an immobilized microorganism amount (the number of copies of target gene per 1 g of carrier) of $1.9 \times 10^9$, which indicates that a large number of microorganisms are immobilized. In contrast, in the carriers Z1 to Z4, the deviation of zeta potential from the zeta potential of nitrifying bacteria is relatively large. Therefore, microorganisms are difficult to be immobilized to the carrier. Moreover, because the carriers Z1 to Z4 do not have continuous pores, the number of immobilized sites of microorganisms is smaller. Thus, the carriers Z1 to Z3 have an immobilized microorganism amount of $1.9 \times 10^8$, which indicates that not many microorganisms are immobilized. The carriers Z4 and Z5 were degraded because their strength was low, so it was unable to measure the immobilized microorganism amount.

Furthermore, the carriers A1 to A3 showed high strength (contact strength in water). In particular, the carrier A1 showed an extremely high strength. On the other hand, although the carrier Z3 showed high strength, the carriers Z1, Z2, Z4, and Z5 showed low strength. In particular, the carriers Z4 and Z5 showed extremely low strength.

Moreover, the carriers A1 to A3 showed high floating capability. In particular, the carrier A1 showed an extremely high floating capability. On the other hand, although the carriers Z1 to Z3 showed high floating capability, the carrier Z4 showed low floating capability.

Here, natural graphite used for the carrier Z2 contains a large amount of metal impurities, and carbon nanotubes used for the carrier Z3 is extremely costly relative to artificial graphite. Therefore, isotropic graphite (artificial graphite) used for the carrier Z1 is the most suitable material as the carbon component used for the carrier. However, the following should be taken into consideration, not merely using isotropic graphite. Even when isotropic graphite is used, the strength or the floating capability may be degraded, continuous pores may not be formed, and moreover microorganisms may be difficult to be immobilized to the carrier (from comparison of the carrier A1 with the carriers Z1 and Z2) if all the isotropic graphite particles have an excessively large or excessively small particle size. For this reason, it is undesirable that all the isotropic graphite particles have an excessively large or excessively small particle size.

Moreover, if the proportion of polyvinyl alcohol, which has a large number of hydrophilic groups, is too high, the zeta potential is decreased, the continuous pores are not formed, and further, microorganisms are difficult to be immobilized to the carrier (see the carrier Z3), although the strength may improve. On the other hand, if the proportion of polyvinyl alcohol is too low, the strength and the floating capability are significantly lowered, and continuous pores are not formed, although the zeta potential may become slightly higher. In addition, because the carrier was degraded immediately after put into water, so the microorganism immobilized amount was unable to be measured (see the carrier Z4). Taking these matters into consideration, it is desirable that the proportion of polyvinyl alcohol be from 20 weight % to 40 weight %.

It should be noted that when phosphoric acid was used for the cross-linking agent, the cross-linking reaction did not take place sufficiently, so nothing became clear through the experiment except that the strength was low.

Second Embodiment

Example 1

The paste shown in Example 1 of the first embodiment was agitated with a foaming machine, and thereafter drawn into a rod shape with an extractor, and subjected to a heat treatment at 150° C. for 18 hours. Thereafter, the resultant material was cut into pellet form with a size of 5 mm square to 10 mm square, to fabricate a microorganism immobilized carrier.

The microorganism immobilized carrier fabricated in this manner is hereinafter referred to as a carrier B1.

Example 2

A microorganism immobilized carrier was fabricated in the same manner as described in Example 1 of the second embodiment, except that, when preparing the paste, starch (manufactured by Wako Pure Chemical Corp., model number 196-13185) was added as a pore forming agent in a weight ratio polyvinyl alcohol:starch=5:1, and that the resultant pellets were washed with hot water at 90° C. for 5 hours to remove the starch as the pore forming agent.

The microorganism immobilized carrier fabricated in this manner is hereinafter referred to as a carrier B2.

Example 3

In the paste prepared according to Example 1 of the first embodiment, formaldehyde (manufactured by Wako Pure Chemical Corp., model number 064-00406) was used in place of citric acid as the cross-linking agent so that the weight ratio polyvinyl alcohol:formaldehyde=2:1, and in addition, starch was added as a pore forming agent so that the weight ratio polyvinyl alcohol:starch=5:1. Next, this paste was put into a beaker and cured at 60° C. for 22 hours, and thereafter, the sample was washed with distilled water. Furthermore, the sample was washed with hot water at 90° C. for 5 hours to remove the starch as the pore forming agent. Thereafter, the resultant material was cut into pellet form with a size of 5 mm square to 10 mm square, to fabricate a microorganism immobilized carrier.

The microorganism immobilized carrier fabricated in this manner is hereinafter referred to as a carrier B3.

Experiment

Using the above-described carriers A1 and B1 to B3, experiments were conducted for the following measurements: (1) Measurement of zeta potential to (7) Measurement of the number of copies of target gene per 1 g of carrier. The results are shown in Table 2 below.

(1) Bulk Density 30 g of dried sample (each carrier) was weighed, placed into a 500-mL beaker, and tapped 100 times. After the tapping, the volume of the sample was measured to obtain the bulk density.

(2) Water Absorption Rate 30 g of the dried sample (each carrier) was weighed and placed into a 500-mL beaker, and thereafter, 300 mL of water was put into the beaker. Next, the two substances were stirred sufficiently in the beaker, allowed to stand still for 24 hours, and lightly drained, and thereafter the weight was measured. Then, the water absorption rate was obtained from the following equation (B).

Water absorption rate=[(Carrier weight after experiment−Carrier weight before experiment)/Carrier weight before experiment]×100 (B)

(3) Swelling Rate

After being subjected to the measurement of water absorption rate, the sample was placed into a 500-mL beaker and tapped 100 times, and thereafter, the volume was measured. Then, the swelling rate was obtained from the following equation (C).

Swelling rate=[1+(Carrier volume after experiment−Carrier volume before experiment)/Carrier volume before experiment]×100     (C)

(4) Durability

After being subjected to the swelling rate measurement, the sample was placed into a 3-L beaker, and thereafter, 2.5 L of water was put into the beaker. Next, a stirring blade was placed at a height corresponding to 2 L (at a position about a ⅔ height from the bottom wall of the beaker) and the sample was stirred at 300 rpm for 24 hours. The weight before and after the stirring was measured, and the durability (weight retention rate) was calculated from the following equation (D).

Weight retention rate=(Weight after stirring/Weight before starring)×100     (D)

(5) Sedimentation Property

A dried sample (each carrier) was allowed to stand still in water for 24 hours. Thereafter, the proportion of the sample sedimented at the bottom of the beaker was determined. Specifically, the sedimentation property was calculated from the following equation (E).

Sedimentation property=Weight of sample sedimented at the bottom of the beaker/Total weight of sample)×100     (E)

(6) Zeta Potential

The measurement was conducted in the same manner as described in the experiment shown in the first embodiment.

(7) Measurement of the Number of Copies of Target Gene Per 1 g of Carrier

The measurement was conducted in the same manner as described in the experiment shown in the first embodiment.

however, that the carrier B1 showed a lower swelling rate and a lower durability. The sedimentation property was also lower.

The carrier B2, which used starch as the pore forming agent, showed a higher bulk density, a higher swelling rate, a higher durability, and a higher sedimentation property than the carrier B1. On the other hand, the water absorption rate was lower.

It was also observed that the carrier B3, in which the cross-linking agent was changed to formaldehyde and the amount of the added cross-linking agent was increased (PVA and isotropic graphite powder were reduced in amount) relative to the carrier B2, showed a remarkably higher water absorption rate than the carrier B2. Although the bulk density was slightly lower than the carrier B2, the swelling rate, the durability, and the sedimentation property were almost equal.

INDUSTRIAL APPLICABILITY

The present invention is applicable to a wastewater treatment apparatus that uses nitrifying bacteria or the like.

The invention claimed is:

1. A microorganism immobilized carrier, characterized by comprising a carbon component and a resin, having a zeta potential of from −25 mV to 0 mV, and containing microorganisms adhered to a surface thereof and/or an interior thereof,
   wherein the carbon component has a particle size of 2 μm to 500 μm, and
   the proportion of the carbon component is from 50 weight % to 75 weight %, and the proportion of the resin is from 25 weight % to 35 weight %.

TABLE 2

|  |  | Carrier A1 | Carrier B1 | Carrier B2 | Carrier B3 |
|---|---|---|---|---|---|
| Material and composition | PVA |  | 30 wt. % |  | 27 wt. % |
|  | Isotropic graphite powder (2 μm-500 μm) |  | 65 wt. % |  | 59 wt. % |
|  | Supplemental remark about manufacturing method | N/A | Agitation with foaming machine + pelletized with extractor | | |
|  | Starch (Weight ratio of PVA:Starch) | N/A |  | Yes (5:1) |  |
|  | Citric acid |  | 5 wt. % |  | — |
|  | Formaldehyde |  | — |  | 14 wt. % |
| Physical property | Bulk density (g/cc) | 0.6 | 0.18 | 0.3 | 0.2 |
|  | Water absorption rate (wt. %) | 191 | 392 | 206 | 402 |
|  | Swelling rate (vol. %) | 140 | 119 | 130 | 133 |
|  | Durability (wt. %) | 97 | 90 | 97 | 98 |
|  | Sedimentation property (wt. %) | 90 | 0 | 90 | 90 |
|  | Zeta potential (mV) | −9.1 | −18.3 | −19.2 | −16.4 |
|  | Number of copies of target gene per 1 g of carrier | $1.9 \times 10^9$ | $1.9 \times 10^9$ | $1.9 \times 10^9$ | $1.9 \times 10^9$ |

As clearly seen from Table 2 above, it is observed that the carrier B1 showed a lower bulk density and a higher water absorption rate than the carrier A1. This is believed to indicate that a large number of pores are formed inside the carrier by agitating the paste with a foaming machine and thereafter preparing pellets by drawing. It should be noted, 2. The microorganism immobilized carrier according to claim 1, wherein the interior thereof includes continuous pores, and the pores have a diameter of from 1 μm to 1000 μm.

3. The microorganism immobilized carrier according to claim 1, wherein the carbon component is graphite.

4. The microorganism immobilized carrier according to claim 1, wherein the microorganisms are nitrifying bacteria.

5. The microorganism immobilized carrier according to claim 1, wherein
the resin is a thermoplastic resin having a hydroxy group, and
the microorganism immobilized carrier further comprises a cross-linking agent for the thermoplastic resin, the cross-linking agent being a chemical compound having a carboxyl group and/or an aldehyde group.

6. The microorganism immobilized carrier according to claim 1, wherein the proportion of the carbon component is from 65 weight % to 75 weight %.

7. The microorganism immobilized carrier according to claim 1, wherein the bulk density is 0.6 g/cc or less.

8. A microorganism immobilized carrier, characterized by comprising a carbon component and a resin, having a zeta potential of from −25 mV to 0 mV, and containing microorganisms adhered to a surface thereof and/or an interior thereof,
wherein the carbon component is isotropic graphite,
the proportion of the carbon component is from 50 weight % to 75 weight %, and the proportion of the resin is from 25 weight % to 35 weight %, and
the carbon component has a particle size of 2 μm to 500 μm.

9. The microorganism immobilized carrier according to claim 8, wherein
the resin is a thermoplastic resin having a hydroxy group, and
the microorganism immobilized carrier further comprises a cross-linking agent for the thermoplastic resin, the cross-linking agent being a chemical compound having a carboxyl group and/or an aldehyde group.

\* \* \* \* \*